United States Patent

Fuchs

[11] Patent Number: 5,952,493
[45] Date of Patent: Sep. 14, 1999

[54] METHOD OF PURIFYING ε-CAPROLACTAM

[75] Inventor: Eberhard Fuchs, Frankenthal, Germany

[73] Assignee: BASF Aktiengesellschaft, Ludwigshafen, Germany

[21] Appl. No.: 09/202,094

[22] PCT Filed: Jun. 13, 1997

[86] PCT No.: PCT/EP98/03098

§ 371 Date: Dec. 9, 1998

§ 102(e) Date: Dec. 9, 1998

[87] PCT Pub. No.: WO97/47596

PCT Pub. Date: Dec. 18, 1997

[30] Foreign Application Priority Data

Jun. 13, 1996 [DE] Germany .................... 196 23 662

[51] Int. Cl.$^6$ .................... C07D 201/16; C07D 223/10
[52] U.S. Cl. .................... 540/540
[58] Field of Search .................... 540/540

[56] References Cited

U.S. PATENT DOCUMENTS

| | | | |
|---|---|---|---|
| 2,752,336 | 6/1956 | Boon | 260/239 |
| 2,786,052 | 3/1957 | Kampschmidt | 260/239 |
| 3,239,490 | 3/1966 | Gee et al. | 260/78 |
| 4,248,781 | 2/1981 | Horn et al. | 260/239 |
| 4,563,308 | 1/1986 | Plantema et al. | 260/239 |
| 4,963,672 | 10/1990 | Merger et al. | 540/538 |
| 5,493,021 | 2/1996 | Barratt et al. | 540/539 |
| 5,502,184 | 3/1996 | Kajikuri et al. | 540/536 |
| 5,539,106 | 7/1996 | Thijert et al. | 540/540 |
| 5,646,277 | 7/1997 | Fuchs et al. | 540/539 |
| 5,739,324 | 4/1998 | Fuchs et al. | 540/539 |

FOREIGN PATENT DOCUMENTS

| | | |
|---|---|---|
| 138241 | 4/1985 | European Pat. Off. . |
| 75083 | 12/1968 | Germany . |
| 51-138690 | 5/1975 | Japan . |
| 60021145 | 7/1983 | Japan . |
| 326165 | 1/1958 | Switzerland . |
| 944307 | 12/1963 | United Kingdom . |
| 969993 | 9/1964 | United Kingdom . |

OTHER PUBLICATIONS

Weissermel et al., *Ind. Org. Chem*, 4th ed, p.272.

*Primary Examiner*—Mukund J. Shah
*Assistant Examiner*—Bruck Kifle
*Attorney, Agent, or Firm*—Keil & Weinkauf

[57] ABSTRACT

Crude caprolactam is purified by reaction with a complex hydride of boron or of aluminum.

4 Claims, No Drawings

METHOD OF PURIFYING ε-CAPROLACTAM

DESCRIPTION

The present invention relates to a process for purifying ε-caprolactam.

ε-Caprolactam is an important starting material for the production of polyamides (nylon 6). There are various ways of producing it industrially. The most popular option is by Beckmann rearrangement of cyclohexanone oxime (K. Weissermel, H. J. Arpe, Industrielle Organische Chemie, 4th edition, pp. 272). Alternatively, cyclohexanecarboxylic acid is produced from toluene via benzoic acid and rearranged with nitrosylsulfuric acid to the ε-caprolactam. Other processes are based on the cyclization of ω-aminocaproic acid derivatives, for example 6-aminocaproic esters (EP-A 376 123) or 6-aminocapronitrile (EP 659 741), in the presence of suitable, typically acidic, catalysts to form ε-caprolactam.

All ε-caprolactam processes give rise to by-products, the nature and quantity of which depend on the principle of the process, on the quality of the starting materials and also on the process parameters. On the other hand, the ε-caprolactam has to meet high purity requirements, especially in fibermaking. For this reason, each manufacturing process requires its own optimized purification process. The various purification processes are cited for example in Process Economics Program Report No. 41 B, Caprolactam and Nylon 6, March 1988, pp. 69.

These purification processes are generally combinations of extraction, distillation and/or crystallization processes. Highly contaminated caprolactam fractions, for example caprolactam purification residues, are frequently subjected to a catalytic hydrogenation. Removal of the catalyst is generally followed by a distillative workup or the return into the purification cycle. In the case of a catalytic suspension hydrogenation of the crude ε-caprolactam using Raney nickel (EP-A-138 241, JP-A-60-21145) the removal of the catalyst presents problems. In the case of a hydrogenation of the crude ε-caprolactam over fixed-bed catalysts (DE-A-1004616, DD-A-75083), decreasing activity or poisoning of the catalysts is likely over time.

It is an object of the present invention to provide a low-cost universally deployable purification process for ε-caprolactam.

We have found that this object is achieved, surprisingly, by using a complex hydride of aluminum or of boron.

The present invention accordingly provides a process for purifying ε-caprolactam, which comprises reacting crude ε-caprolactam with a complex hydride of aluminum or of boron.

Suitable complex hydrides of aluminum or of boron for the process of this invention are in particular sodium borohydride, lithium borohydride, potassium borohydride, calcium borohydride, sodium cyanoborohydride, sodium methoxyethoxyaluminum hydride, lithium tri-t-butoxyaluminum hydride.

The amount of hydride hydrogen used naturally depends on the concentration of the impurities in the ε-caprolactam. It is chosen so that an excess of hydride hydrogen is present, based on the impurities to be reduced. Preference is given to an excess of from 1.5 to five times, based on the stoichiometrically required hydride quantity.

It has been found that, to obtain an adequate reaction rate in the ε-caprolactam purification process of this invention, from 10 to 50% by weight of water, based on crude ε-caprolactam, has to be added to the reaction mixture when a borohydride is used.

In a preferred embodiment, the reaction is carried out in the presence of from 0.5 to 5 mol %, in particular from 1 to 4 mol % of $NaBH_4$ and of from 10 to 50% by weight of water, based on crude ε-caprolactam. The sodium borohydride can be used in solid form or in the form of a commercially available aqueous solution.

The reaction is preferably carried out within the range from 10 to 150° C., in particular within the range from 20 to 100 ° C. The reaction time is within the range from 0.5 h to 200 h, preferably within the range from 1 h to 100 h.

After the reaction has ended, water and the reduced impurities are distilled off under a slightly reduced pressure. It is also possible to distil off water and impurities continuously even during the reaction by applying a slight reduced pressure. Thereafter the reaction mixture is subjected to a conventional distillation under reduced pressure (0.5–8 mm Hg). Pure ε-caprolactam is obtained as distillate with a UV number<10 (see below).

The process of this invention is suitable for purifying ε-caprolactam produced by any of the conventional manufacturing processes. This process is advantageously suitable for purifying ε-caprolactam produced by cyclization of ω-aminocaproic acid derivatives, for example ω-aminocaproic acid, ω-aminocaproamide, ω-aminocaproic ester and ω-aminocapronitrile.

EXAMPLES

Purification of a Caprolactam Produced by Cyclization of ω-aminocapronitrile

The purity of the ε-caprolactam is determined in terms of the UV number. The UV number is defined as the sum of all absorbances of a 50% strength by weight aqueous caprolactam solution measured at intervals of 10 nm in the wavelength range from 280 nm to 400 nm in a cell having a pathlength of d=5 cm. The UV number of the purified ε-caprolactam should not exceed 10.

Example 1

Preparation of ε-caprolactam in Accordance with DE-A 43 396 48

100 parts by weight of ω-aminocapronitrile were dissolved in 1000 parts by weight of ethanol and 30 parts by weight of water and passed over a fixed bed of titania (anatase) at 220° C. with a residence time of 12 min. The solvent was then distilled off. The crude caprolactam thus obtained was used in the following purification stage.

Purification of the Crude ε-caprolactam 70 parts by weight of crude caprolactam and 30 parts by weight of water were admixed with 1% by weight of sodium borohydride (based on crude ε-caprolactam) in a stirred vessel equipped with a still head. After 100 h, the reaction mixture was subjected to fractional distillation. ε-Caprolactam passed over at 119° C. (2 mbar) with a UV number of 3.1.

Example 2

Crude caprolactam prepared by Beckmann rearrangement (see Process Economics Program Report (SRI Report) No. 41 B, Caprolactam and Nylon 6, March 1988) was reacted as described in Example 1 in the presence of 0.4% by weight $NaBH_4$. After 24 h, the reaction mixture was subjected to fractional distillation. ε-Caprolactam passed over at 125° C. (3 mbar) with a UV number of 3.5.

I claim:

1. A process for purifying ε-caprolactam, which comprises reacting ε-caprolactam with a complex hydride of aluminum or of boron acidic substances.

2. A process as claimed in claim 1, wherein the complex hydride is selected from the group consisting of $NaBH_4$, $LiBH_4$, $KBH_4$, $Ca(BH_4)_2$, and $NaBH_3CN$.

3. A process as claimed in claim 1, wherein from 2 to 20 mol % of hydridic hydrogen is used, based on the ε-caprolactam to be purified.

4. A process as claimed in claim 1, wherein ε-caprolactam is reacted in the presence of from 0.5 to 5 mol % of $NaBH_4$ and from 10 to 50% by weight of water, based on the ε-caprolactam to be purified.

* * * * *

UNITED STATES PATENT AND TRADEMARK OFFICE
CERTIFICATE OF CORRECTION

PATENT NO.: 5,952,493

DATED: September 14, 1999

INVENTOR(S): FUCHS et al.

It is certified that error appears in the above-identified patent and that said Letters Patent is hereby corrected as shown below:

Col. 2, claim 1, last line, delete "acidic substances".

Signed and Sealed this

Thirtieth Day of May, 2000

Attest:

Q. TODD DICKINSON

Attesting Officer      Director of Patents and Trademarks

UNITED STATES PATENT AND TRADEMARK OFFICE
CERTIFICATE OF CORRECTION

PATENT NO. : 5,952,493
DATED : September 14, 1999
INVENTOR(S) : Eberhard Fuchs

It is certified that error appears in the above-identified patent and that said Letters Patent is hereby corrected as shown below:

Column 2,
Line 67, "aluminum or of boron" should be -- boron in the absence of acidic substances --.
Line 67, delete "acidic substances".

Signed and Sealed this

Sixth Day of July, 2004

JON W. DUDAS
*Acting Director of the United States Patent and Trademark Office*